(12) United States Patent
Palti

(10) Patent No.: US 11,471,544 B2
(45) Date of Patent: Oct. 18, 2022

(54) USING A STEERABLE BEAM OF RF ENERGY TO ELIMINATE VIRUSES AND/OR BACTERIA FROM A VOLUME OF AIR

(71) Applicant: Yoram Palti, Haifa (IL)

(72) Inventor: Yoram Palti, Haifa (IL)

( * ) Notice: Subject to any disclaimer, the term of this patent is extended or adjusted under 35 U.S.C. 154(b) by 33 days.

(21) Appl. No.: 17/316,260

(22) Filed: May 10, 2021

(65) Prior Publication Data
US 2021/0353787 A1 Nov. 18, 2021

Related U.S. Application Data

(60) Provisional application No. 63/023,496, filed on May 12, 2020.

(51) Int. Cl.
*H01Q 3/26* (2006.01)
*A61L 2/00* (2006.01)
*A61L 2/24* (2006.01)
*H04B 7/06* (2006.01)

(52) U.S. Cl.
CPC .............. *A61L 2/0064* (2013.01); *A61L 2/24* (2013.01); *H01Q 3/26* (2013.01); *H04B 7/0617* (2013.01)

(58) Field of Classification Search
CPC . A61L 2/00; A61L 2/0064; A61L 2/08; A61L 2/24; A61L 2/12; H01Q 3/22; H01Q 3/24; H01Q 3/26; H01Q 3/34; H01Q 3/36; H01Q 3/40; H01Q 21/00; H01Q 21/06; H01Q 3/385; H04B 7/0617
See application file for complete search history.

(56) References Cited

U.S. PATENT DOCUMENTS

| | | | | |
|---|---|---|---|---|
| 4,566,013 A * | 1/1986 | Steinberg | ................. | H01Q 3/42 342/372 |
| 5,162,803 A * | 11/1992 | Chen | .................... | H01Q 13/085 342/372 |
| 5,977,910 A * | 11/1999 | Matthews | .............. | H01Q 25/00 342/368 |
| 6,426,721 B1 * | 7/2002 | Obara | .................. | H01Q 3/2676 342/372 |
| 6,504,505 B1 * | 1/2003 | Yung | ........................ | H01Q 3/26 342/374 |
| 9,433,692 B2 * | 9/2016 | Hyde | ........................ | A61L 2/08 |
| 11,398,683 B2 * | 7/2022 | Adams | ..................... | H01Q 3/34 |

* cited by examiner

*Primary Examiner* — Tho G Phan
(74) *Attorney, Agent, or Firm* — Potomac Law Group, PLLC

(57) ABSTRACT

Pathogens (e.g., viruses or bacteria) within a volume of air can be killed or deactivated using RF energy. A plurality of phase shifters input an RF signal and output a phase-shifted version of the RF signal at their respective outputs, wherein an amount of phase shift introduced by each of the phase shifters is controllable. A phased array antenna has a plurality of microwave radiators, and each of the respective outputs of the phase shifters drives a respective one of the microwave radiators. A controller controls the phase shifters to drive the phased array antenna such that a beam of RF energy emanates from the phased array antenna and sweeps through a volume positioned in front of the phased array antenna, and the beam of RF energy kills or deactivates the pathogens.

17 Claims, 7 Drawing Sheets

Reassessment of RF Exposure Limits & Policies, and Proposed Changes in the Rules Regarding Human Exposure to RF Fields FCC 2013 Limits for Maximum Permissible Exposure (MPE)

| Frequency range (MHz) | Electric field strength (V/m) | Magnetic field strength (A/m) | Power density (mW/cm2) | Averaging time (minutes) |
|---|---|---|---|---|
| (A) Limits for Occupational/Controlled Exposure | | | | |
| 0.3 - 3.0 | 614 | 1.63 | 100* | 6 |
| 3.0 - 30 | 1842/f | 4.89/f | 900/f2* | 6 |
| 30 - 300 | 61.4 | 0.163 | 1.0 | 6 |
| 300 - 1,500 | - | - | f/300 | 6 |
| 1,500 - 1,00,000 | - | - | 5 | 6 |
| (B) Limits for General Population/Uncontrolled Exposure | | | | |
| 0.3 - 1.34 | 614 | 1.63 | 100* | 30 |
| 1.34 - 30 | 824/f | 2.19/f | 180/f2* | 30 |
| 30 - 300 | 27.5 | 0.073 | 0.2 | 30 |
| 300 - 1,500 | - | - | f/1500 | 30 |
| 1,500 - 1,00,000 | - | - | 1.0 | 30 |

[1] FCC uses different units than ICNIRP for power density: mW/cm2 and not W/m2; W/m2 = 0.1 mW/cm2

FIG. 1
PRIOR ART

USING A STEERABLE BEAM OF RF ENERGY TO ELIMINATE VIRUSES AND/OR BACTERIA FROM A VOLUME OF AIR

CROSS REFERENCE TO RELATED APPLICATIONS

This application claims the benefit of U.S. Provisional Application 63/023,496, filed May 12, 2020, which is incorporated herein by reference in its entirety.

BACKGROUND

Viruses, bacteria, and/or other microorganisms (collectively referred to herein as "pathogens") that are suspended in a volume of air can be killed or deactivated by exposing them to RF energy. But exposing the pathogens to RF energy is problematic because when the RF energy is strong enough to kill or deactivate the pathogens, it can be unsafe for people (or at least exceed relevant government rules). FIG. 1 is a prior art table that shows the FCC's limits for maximum permissible exposure to RF energy.

SUMMARY OF THE INVENTION

One aspect of the invention is directed to a first apparatus for killing or deactivating pathogens within a volume of air. The first apparatus comprises an RF signal generator, a plurality of phase shifters, a phased array antenna, and a controller. The RF signal generator generates a first RF signal at a frequency F, wherein the frequency F is between 1 and 20 GHz. Each of the phase shifters inputs the first RF signal and outputs a phase-shifted version of the first RF signal at a respective output, wherein an amount of phase shift introduced by each of the plurality of phase shifters is controllable based on a state of at least one control input. The phased array antenna has a plurality of microwave radiators, and each of the respective outputs of the plurality of phase shifters drives a respective one of the plurality of microwave radiators. The controller is programmed to control the state of the at least one control input so that the plurality of phase shifters drives the phased array antenna such that a beam of RF energy emanates from the phased array antenna and sweeps through a volume positioned in front of the phased array antenna, the volume having an outer boundary with an area A, wherein the beam has an area B, an irradiance flux density D, and a speed V, all measured at the outer boundary. B and D are large enough and V is small enough such that each voxel in the volume is irradiated by the beam of RF energy for enough time during each scan to kill or deactivate pathogens suspended within the volume. And D and a ratio of B/A are small enough so that the power density measured at the outer boundary, averaged over time, is (a) less than F/300 mW/cm² and (b) less than 5 mW/cm².

In some embodiments of the first apparatus, D and a ratio of B/A are small enough so that the power density measured at the outer boundary, averaged over time, is (a) less than F/1500 mW/cm² and (b) less than 1 mW/cm². In some embodiments of the first apparatus, B and D are large enough and V is small enough such that each voxel in the volume is irradiated by the beam of RF energy for enough time during each scan to heat pathogens suspended within the volume by at least 50° C.

In some embodiments of the first apparatus, the outer boundary of the volume is at least 10 cm away from the phased array antenna. In some embodiments of the first apparatus, the outer boundary of the volume is at least 30 cm away from the phased array antenna.

In some embodiments of the first apparatus, B and D are large enough and V is small enough such that each voxel in the volume is irradiated by the beam of RF energy for enough time during each scan to heat microdroplets suspended within the volume by at least 50° C., wherein the microdroplets include (i) pathogens and (ii) water, and wherein the microdroplets are small enough to remain suspended within the volume.

In some embodiments of the first apparatus, B and D are large enough and V is small enough such that each voxel in the volume is irradiated by the beam of RF energy for enough time during each scan to heat microdroplets suspended within the volume by at least 50° C., wherein the microdroplets include (i) pathogens and (ii) water, and wherein the microdroplets have volumes of less than $10^{12}$ Liter.

In some embodiments of the first apparatus, the beam of RF energy sweeps through the entire volume positioned in front of the phased array antenna at least once per second. In some embodiments of the first apparatus, the beam of RF energy sweeps through the entire volume positioned in front of the phased array antenna at least 100 times per second. In some embodiments of the first apparatus, the RF signal generator comprises a circuit that generates a low-power RF signal and an amplifier configured to generate the first RF signal by amplifying the low-power RF signal.

Some embodiments of the first apparatus further comprise a battery. In these embodiments, the RF signal generator, the plurality of phase shifters, and the controller are powered by the battery.

In some embodiments of the first apparatus, the pathogens comprise bacteria. In some embodiments of the first apparatus, the pathogens comprise viruses.

Another aspect of the invention is directed to a second apparatus for killing or deactivating pathogens within a volume of air. The second apparatus comprises an RF signal generator, a plurality of phase shifters, a phased array antenna, and a controller. The RF signal generator generates a first RF signal at a frequency F, wherein the frequency F is between 1 and 20 GHz. Each of the phase shifters inputs the first RF signal and outputs a phase-shifted version of the first RF signal at a respective output, wherein an amount of phase shift introduced by each of the plurality of phase shifters is controllable based on a state of at least one control input. The phased array antenna has a plurality of microwave radiators, and each of the respective outputs of the plurality of phase shifters drives a respective one of the plurality of microwave radiators. The controller is programmed to control the state of the at least one control input so that the plurality of phase shifters drives the phased array antenna such that a beam of RF energy emanates from the phased array antenna and sweeps through a volume positioned in front of the phased array antenna, the volume having an outer boundary, The beam has a total power of $P_B$, a width in the scanning direction of $W_B$, and a sweep velocity of V, all measured at the outer boundary. A single pathogen positioned at the outer boundary has a cross section area of $A_P$. The amount of RF energy that must hit a single pathogen in order to destroy that single pathogen is $E_D$, wherein $V < A_P P_B / W_B E_D$. The power density measured at the outer boundary, averaged over time, is (a) less than F/300 mW/cm² and (b) less than 5 mW/cm².

In some embodiments of the second apparatus, the power density measured at the outer boundary, averaged over time, is (a) less than F/1500 mW/cm² and (b) less than 1 mW/cm².

In some embodiments of the second apparatus, the pathogens comprise bacteria. In some embodiments of the second apparatus, the pathogens comprise viruses.

BRIEF DESCRIPTION OF THE DRAWINGS

FIG. 1 is a prior art table that shows the FCC's limits for maximum permissible exposure to RF energy.

Various embodiments are described in detail below with reference to the accompanying drawings, wherein like reference numerals represent like elements.

DESCRIPTION OF THE PREFERRED EMBODIMENTS

The embodiments described herein advantageously kill or deactivate pathogens within a volume of air without exceeding relevant limits for maximum permissible exposure (MPE). This is accomplished by using a phased array antenna to electronically scan a relatively narrow beam of RF energy through the volume. The narrow beam of RF energy is strong enough and is traveling slow enough so that when the beam traverses any voxels within the volume that contain pathogens, RF energy will be absorbed by the pathogens to an extent that is sufficient to kill or deactivate the pathogens. Notably, the power density averaged over time does not exceed MPE.

FIG. 2 is a block diagram of an apparatus 10 for killing or deactivating pathogens within a volume of air. As used herein, in the context of viruses, deactivating a virus means rendering the virus incapable of infecting a cell or reproducing. The apparatus 10 includes an RF signal generator 30 that generates a first RF signal at a frequency F between 1 and 20 GHz. In some embodiments, the RF signal generator 30 includes a low-power RF signal generator 32 that generates a low-power output signal. In these embodiments, this low-power output signal is amplified by an RF amplifier 34.

The output of the RF signal generator 30 (i.e., the first RF signal) is provided to an array of phase shifters 40. Each of the phase shifters inputs the first RF signal and outputs a phase-shifted version of the first RF signal at a respective output. The amount of phase shift introduced by each of the plurality of phase shifters is controllable based on a state of at least one control input. A phased array antenna 50 includes a plurality of microwave radiators, and each of the respective outputs of the plurality of phase shifters drives a respective one of the plurality of microwave radiators.

A controller 20 is programmed to control the state of the at least one control input (which is provided to the array of phase shifters 40). This causes the plurality of phase shifters 40 to drive the phased array antenna such that a beam of RF energy will emanate from the phased array antenna into a volume 60 positioned in front of the phased array antenna 50. The controller 20 continuously sends appropriate control signals to the array of phase shifters 40 so that the induced phase shifts cause the beam of RF energy to sweep through the volume 60, and the nature of this sweeping is described below.

Optionally, temperature sensors (not shown) may be used to monitor the temperature at the phased array antenna 50. Optionally, an RF power sensor (not shown) may be incorporated to measure the RF power output of the apparatus 10.

The volume 60 has an outer boundary 65, and the apparatus 10 is designed to work effectively within this outer boundary 65. Note that this outer boundary 65 is an imaginary boundary that represents a curved surface with an area A, and the beam of RF energy 55 can continue traveling past this outer boundary 65. As such, the apparatus 10 may also have some efficacy beyond the outer boundary 65.

The beam 55 that emanates from the phased array antenna 50 has an area B measured on the curved surface 65, an irradiance flux density D measured on this curved surface 65, and a speed V respect to this curved surface 65, as represented schematically in FIG. 3. The path of the beam 55 in FIG. 3 is represented by 7 dashed lines. But in practice, there will be a great many more than 7 lines (e.g., on the order of 100-10,000, depending on the area A of the outer boundary 65 and the width of the beam 55) and they will be much more closely spaced.

The area B and the irradiance flux density D are large enough and the velocity V is small enough such that each voxel in the volume is irradiated by the beam of RF energy for enough time during each scan through the volume 60 to kill or deactivate pathogens suspended within the volume (e.g., by heating them by at least 50° C.). One way to achieve this in a case where (i) a single pathogen positioned at the outer boundary has a cross section area of $A_P$ and (ii) the amount of RF energy that must hit a single pathogen in order to destroy that single pathogen is $E_D$ is to make sure that the velocity of the beam satisfies the equation $V<A_P P_B/W_B E_D$, where $P_B$ is the total power of the beam, $W_B$ is the width of the beam in the scanning direction (see FIG. 3), and V is the sweep velocity of the beam, all measured at the outer boundary 65.

In embodiments where people might encounter the beam, the irradiance flux density D and a ratio of the areas B/A are preferably small enough so that the power density measured at the outer boundary, averaged over time, is (a) less than F/300 $mW/cm^2$ and (b) less than 5 $mW/cm^2$ to comply with relevant safety standards.

Note that FIG. 2 only shows the path of the beam at the imaginary curved surface 65. But because the beam is strong enough to kill or deactivate the pathogens at the outer boundary 65, it will also be strong enough to kill or deactivate pathogens at closer-in locations (i.e., locations between the phased array antenna 50 and the outer boundary 65).

The apparatus 10 establishes a 3D volume of space 60 where pathogens that enter it are killed or deactivated. The volume of space 60 is continuously scanned by a narrow RF electromagnetic beam 55. This beam 55 has sufficient energy to heat and elevate the temperature of micro-particles suspended in the air to a level that is sufficient to kill or deactivate them (e.g., in the context of many viruses, by 50° C.).

In some embodiments, the apparatus 10 is powered by a battery 15, and the entire apparatus 10 has a size that is on the same order of magnitude as a typical cell phone. In some embodiments, the apparatus 10 is wearable. The total RF energy generated by the apparatus 10 is similar to that of a common cell phone (i.e., well within the legally permissible transmission levels). The apparatus 10 achieves its effect with an overall very low energy as the whole energy is concentrated into a very narrow beam 55 that is effective in raising the temperature of an ultra-small particle to a destructive level within a very short time. The beam scanning speed is controlled so as to reside at each voxel within the protected zone for a length of time that is sufficient to achieve the desired effect.

Figure 8A:
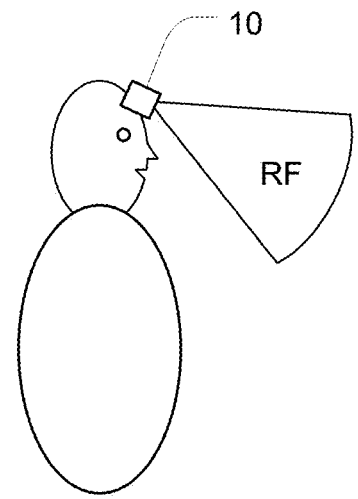
FIGS. 8A and 8B depict examples for positioning the apparatus to protect a person from pathogens that enter the human body via the nose, mouth, or eyes.
Figure 8B:
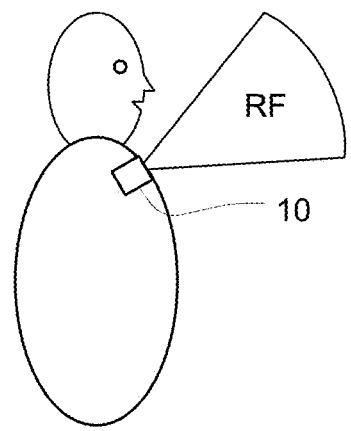

In some embodiments, the protected volume 60 is positioned in front of the face of a person to be protected from infection (e.g., as depicted in FIGS. 8A and 8B). In this case, pathogens that approach the person's face (e.g., by movement of air or movement of the person) can be killed or deactivated before they arrive at potential entry ports (e.g., the mouth, nose, and eyes). As a result, the person will not become infected by the pathogens. The same apparatus 10 may also be used by an infected person to minimize the chance of infecting other people. In this situation, when the person using the apparatus 10 talks, coughs, sneezes, or breathes, the apparatus 10 has an opportunity to kill or deactivate the pathogens as they pass through the volume 60.

The amount of RF energy that must be beamed into the volume 60 in order to have its intended effect will depend on the type of pathogen. More specifically, because the size of viruses is typically on the order of 100 nm while the size of bacteria is typically on the order of 1 μm, significantly more energy is needed to kill bacteria than to kill or deactivate viruses. In some cases, the pathogens may be suspended in microdroplets (e.g., with volumes up to $10^{-12}$ Liter), in which case the amount of energy that will be needed will vary depending on the size of the microdroplets.

We begin by analyzing an example in the context of killing or deactivating viruses to ascertain numeric values for the various parameters involved. For a typical virus, the volume and weight are on the order of $1.5 \times 10^{-21}$ cc and $10^{-21}$ g. The conversion factor between Watts and Calories Per Second=0.2388. The specific heat of protein is 1700 J/kg° C., and the specific heat of water is 4180 J/kg° C. Therefore, to heat protein by 1° you need half the energy (as compared to water). Assuming close to 100% energy absorption, a beam of 1 W will heat 1 g protein by about 0.5° C. in 1 s. To the extent that the energy absorption is less than 100%, all durations of irradiation with RF described herein must be increased by a corresponding factor (e.g., by increasing the power of the beam or decreasing the scanning velocity). Note that many of the numbers in these examples are approximations.

Example with a Beam Width of 0.1 mm

Figure 2:
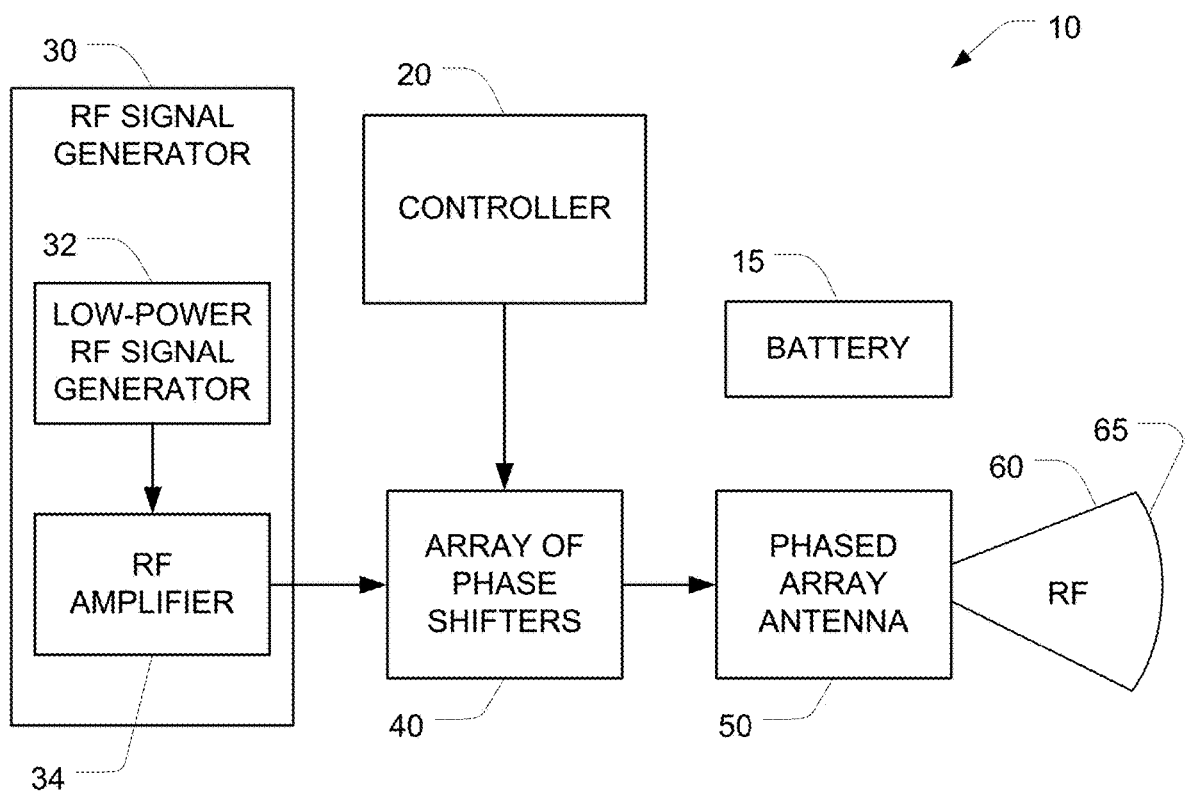
FIG. 2 is a block diagram of an apparatus for killing or deactivating pathogens within a volume of air.
Figure 3:
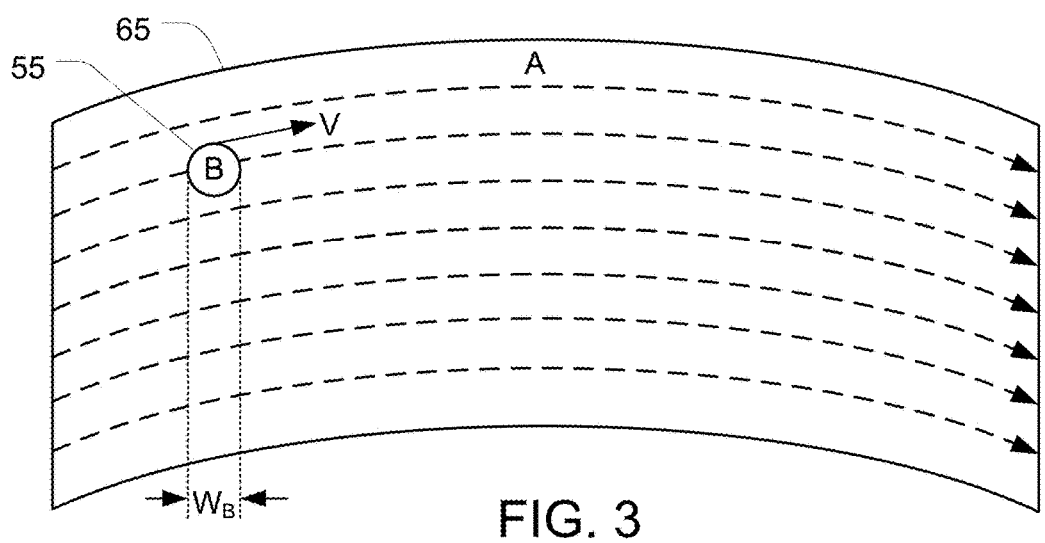
FIG. 3 depicts various characteristics if the beam in the FIG. 2 embodiment.

Referring now to FIGS. 2 and 3, the basis of this example of the apparatus 10 is a 1-10 Watt, 1-20 GHz transmitter that generates an RF beam output to a volume of air 60 contaminated with viruses.

Let us assume we have a 1 Watt RF wave source. Using the phased array antenna 50, the apparatus 10 generates a practically parallel RF beam 55. Assume that the beam has a diameter W of 0.1 mm, such that its area B is $10^{-4}$ cm². The energy density of the beam is therefore $10^4$ W/cm².

The diameter of the coronavirus that causes COVID 19 is 120-180 nm, and the diameter of other viruses can vary widely. But for purposes of discussion, we will assume that the profile area of the virus being targeted has a diameter or long axis of 100 nm, which is $10^{10}$ cm². Assuming that the virus absorbs 100% of the RF energy when it is subjected to the beam 55, it will absorb—$10^4$ w/cm²×$10^{-10}$ cm²=$10^{-6}$ W per virus.

We will also assume that the virus can be killed or deactivated by raising its temperature by 50° C., that the virus weighs $10^{-18}$ g, and that its composition has physical properties similar to those of proteins. In this situation, the heating energy required to elevate the temperature by 1° C. is $0.5 \times 10^{-18}$ calories or $2 \times 10^{-18}$ W×s. Thus, in order to elevate the temperature of the virus by 50° C., we need $2 \times 10^{-18} \times 50 = 1 \times 10^{-16}$ W×s.

Because the available beam energy per virus is $10^{-6}$ W, the time needed for elevating the virus temperature by 50° C. is $10^{-16}/10^{-6} = 10^{-10}$ s. In other words, to destroy the virus, the virus must remain exposed to the beam for $10^{-10}$ s.

The RF beam 55 is scanned within the volume 60. The RF beam formation and the scanning are achieved by the phased array antenna 50, which is driven by the array of phase shifters 40 under control of the controller 20.

The energetic efficacy and effective range depend (in addition to the overall power of the source) on the width of the beam 55 and the scanning beam movement velocity V. For simplicity, we assume in the analysis an energy-uniform square beam with a width W of 0.1 mm.

To obtain the required $10^{10}$ s duration of exposure at the outer boundary 65, the $10^{-2}$ cm width beam ($W_B$ in FIG. 3) needs to scan at a velocity V less than or equal to $10^{-10}$ cm/$10^{-10}$ s (i.e., less than or equal to $10^8$ cm/sec).

If the outer boundary 65 has an area A of 10×10 cm, we have a scan length of 10 cm. And as the beam height is $10^{-2}$ cm, we need 1000 scans to cover the entire area A, for a total scan length of $10 \times 1000 = 10^4$ cm. Thus, assuming we have a 1 W source, a 0.1 mm wide beam and a protected volume with a cross section of 10×10 cm, a scan of the entire volume 60 can be completed in only $10^4$ cm/$10^8$ (cm/s)=$10^{-4}$ sec.

In a variation of this embodiment, If the outer boundary has an area of 100×100 cm we have a scan length of 100 cm and as the beam height is $10^{-2}$ cm, we need 10,000 scans, for a total scan length of 100×10,000=$10^6$ cm. Thus, the required scan time, T, for a 1 W, 0.1 mm wide beam and a 100×100 cm protected area will be 100 times longer than for the 10×10 cm example (i.e., 10' sec for the 100×100 variation).

Note that these values do not change when many viruses are present within the volume 60.

In the example above, the fastest scanning velocity that is appropriate for killing or deactivating the virus particles was calculated at the outer boundary 65 (which is the portion of the scanning volume 60 that is farthest from the phased array antenna 50). For any given scanning beam, the linear velocity V is different at different locations along the beam. More specifically, the velocity of the beam will be faster at positions that are farther away from the source and slower at positions that are closer to the source.

Figure 4:
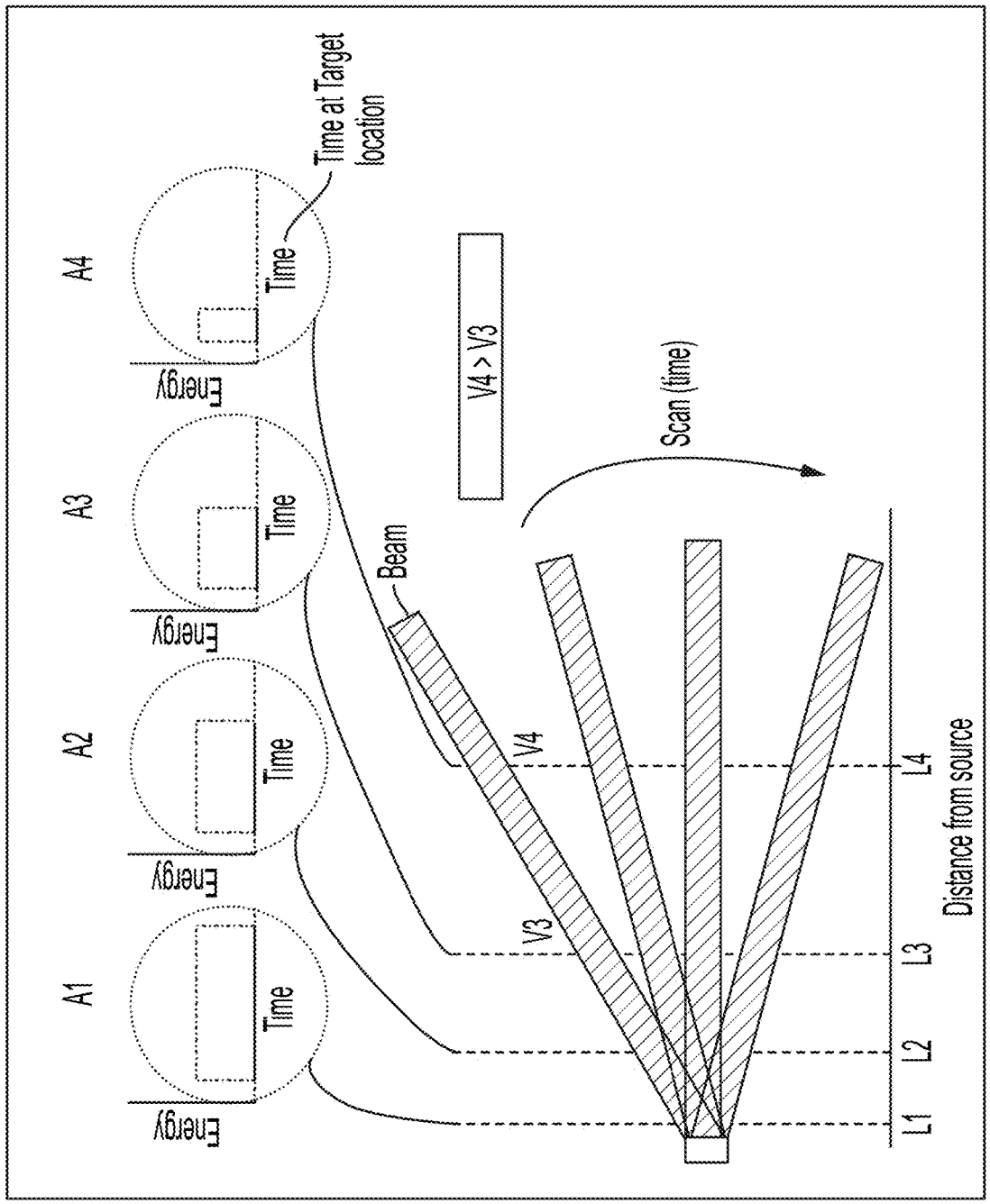
FIG. 4 depicts energy profiles with respect to time at four different distances from the source in the FIG. 2 embodiment.

This is depicted in FIG. 4, which shows the energy profiles with respect to time at four different distances from the source L1, L2, L3, and L4. Notably, at larger distances (L3/A3 and L4/A4), the energy-time product is lower. Thus, for any given target area, the highest energy×time level is closest to the phased array antenna 50 (where the beams originate). In view of this, once it has been determined that the apparatus 10 can kill or deactivate virus particles positioned at the outer boundary 65 (as explained above), we can assume that it will also kill or deactivate virus particles located within the volume 60 (none of which are further from the phased array antenna 50 than the outer boundary 65).

Figure 5:
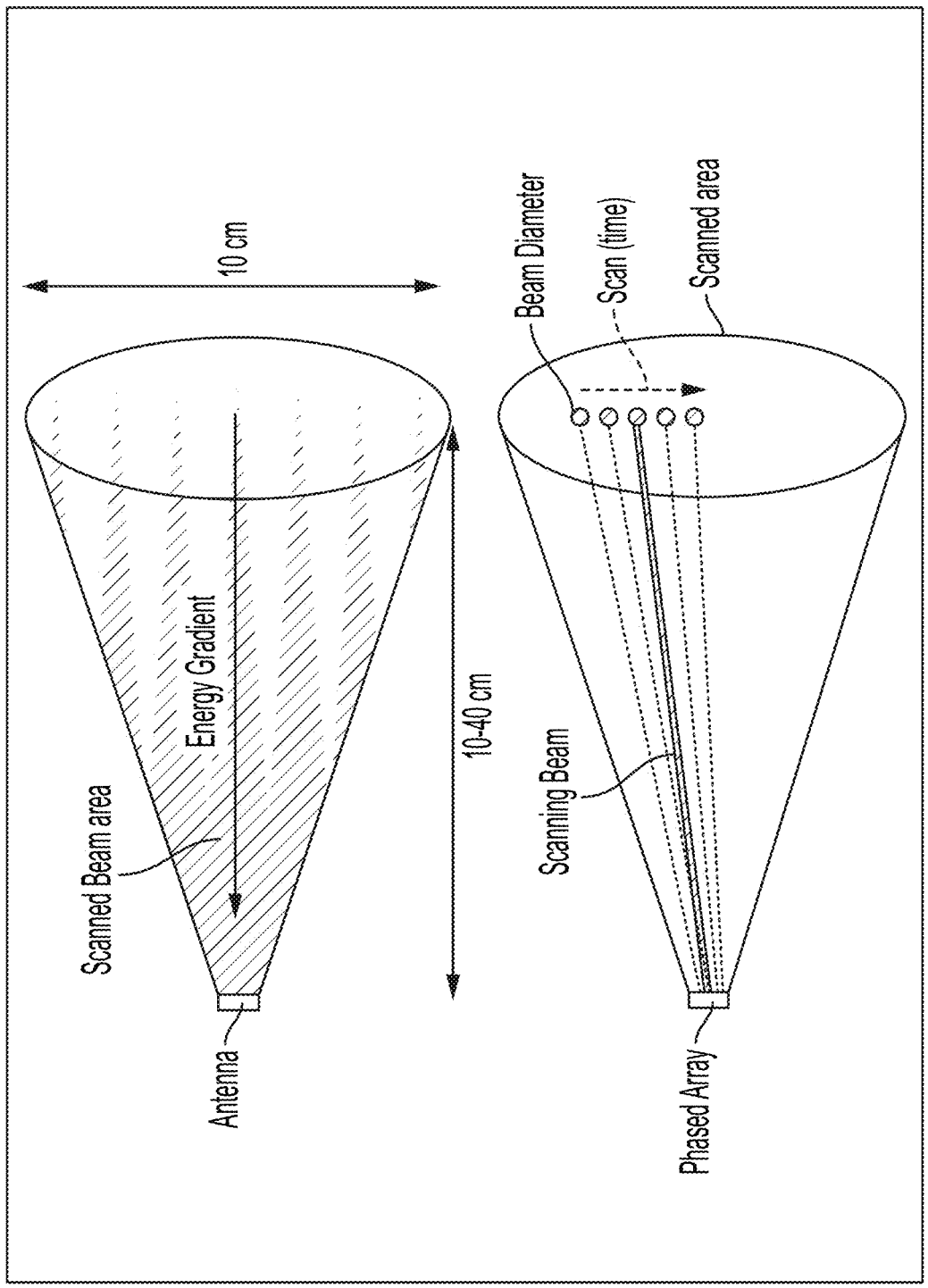
FIG. 5 depicts how the energy gradient increases at positions that are closer to the antenna in the FIG. 2 embodiment.

FIG. 5 depicts how the energy gradient (which is the product of energy×time) increases at positions that are closer to the antenna (with higher values depicted by denser shading and lower values depicted by less dense shading).

The numeric values in the example above can be varied. For example, if the 0.1 mm wide beam in the example above is replaced with a 1 mm wide beam, and the total power in the beam remains constant at 1 W, the 100× increase in beam area will mean that the energy density within the beam decreases by 100×. If the scanning speed remains constant, any given virus particle will be irradiated by the beam for a duration of time that is 10× longer than the example above (because the beam is 10× wider). Thus, in order to ensure that enough energy reaches any given virus particle to heat that virus particle by 50° C., the scanning rate of the beam must be slowed down by a factor of 10 with respect to the example above. But because the spacing between scan lines can be increased by a factor of 10, the total amount of time necessary to complete a scan of the entire outer boundary 65 will remain the same as in the example above.

In some preferred embodiments, the width of the beam 55 ($W_B$ in FIG. 3) is between 0.05 and 5 mm. In some preferred embodiments, $W_B$ is between 0.1 and 1 mm. Note that while a round beam 55 is depicted in FIG. 3, beams with different shapes may be used. Example of suitable shapes for the beam 55 include square beams, rectangular beams, and slit-shaped beams (e.g., oriented so their height is larger than their width $W_B$). In addition, while only a single beam 55 is depicted in FIG. 3, the system can also sweep a plurality of beams through the volume 60 instead of a single beam.

The examples above provide numeric examples in the situation where the pathogens are viruses. But the same apparatus 10 can be used when the pathogens are bacteria or other microorganisms by scaling various parameters (e.g., scaling up the power and/or slowing down the scan velocity) to account for the larger amount of energy that must be absorbed by the pathogens to raise their temperature to a point where the pathogens are killed or deactivated.

In some embodiments, the RF frequency at which the system operates is selected to achieve maximum heating efficiency depending on the target pathogen. For example, if the target pathogen includes a significant amount of water, a frequency of 2.45 GHz may be used.

Some of the examples above assume that the pathogens are destroyed by increasing their temperature to 50° C. above ambient. Note, however, that the magnitude of the increase in temperature required to kill or deactivate the pathogen will depend on the particular pathogen in question. Preliminary data indicates that the SARS-CoV-2 virus is deactivated at 56° C. Therefore, assuming an ambient temperature of 20° C., only a 36° C. rise in temperature is required to deactivate that particular virus. Various parameters can be adjusted to account for this (e.g., decreasing the beam power or increasing the scanning velocity).

Safety Concerns

Figure 6:
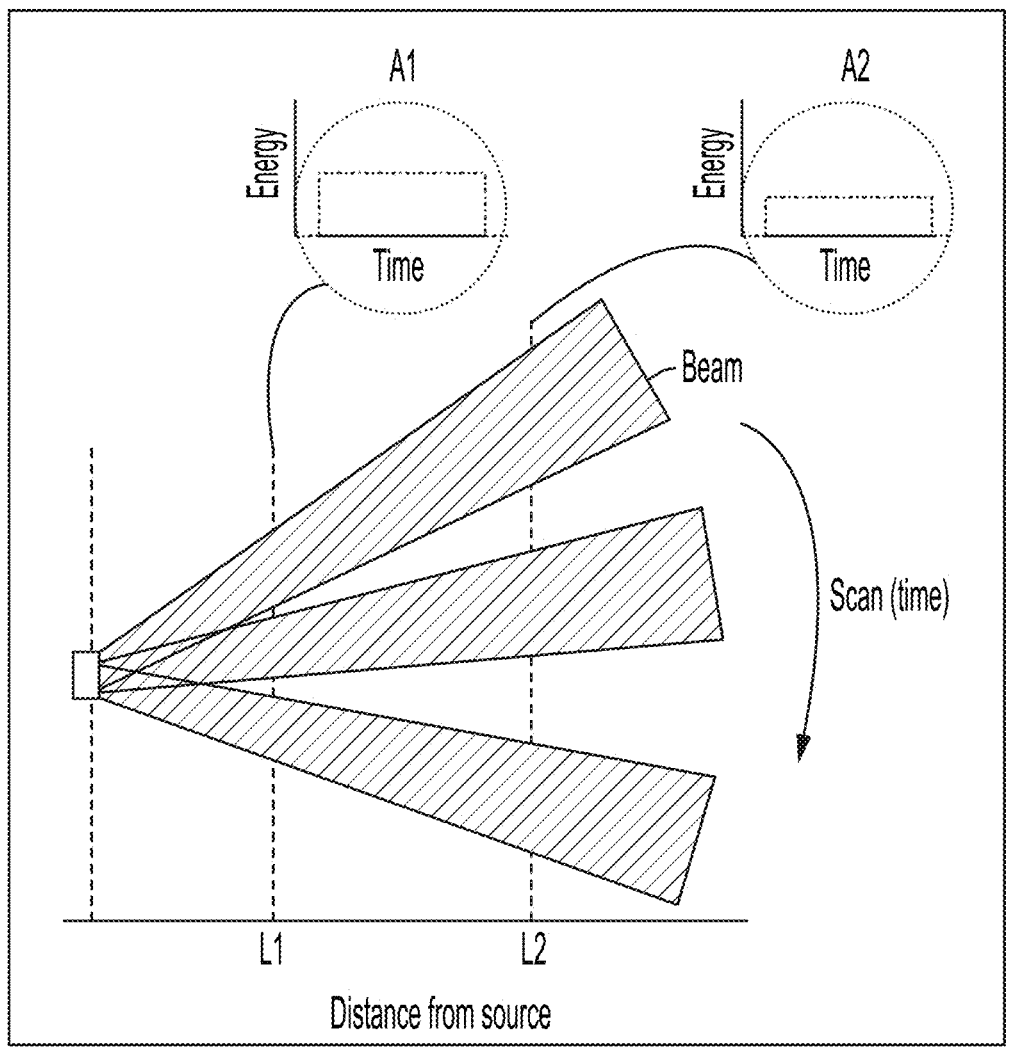
FIG. 6 shows how the field power can be further attenuated with distance from the source by generating diverging beams.

The calculations above assume that the phased array antenna 50 is outputting a parallel beam. As described above in connection with FIGS. 4 and 5, the effective beam RF energy is attenuated with distance. This is due to the fact that the beam movement velocity grows with distance and therefore the dwell time at each location is reduced. Optionally, the field power can be further attenuated with distance from the source by generating diverging, rather than parallel beams, as illustrated in FIG. 6. The divergence angle can be adjusted as needed.

Figure 7:
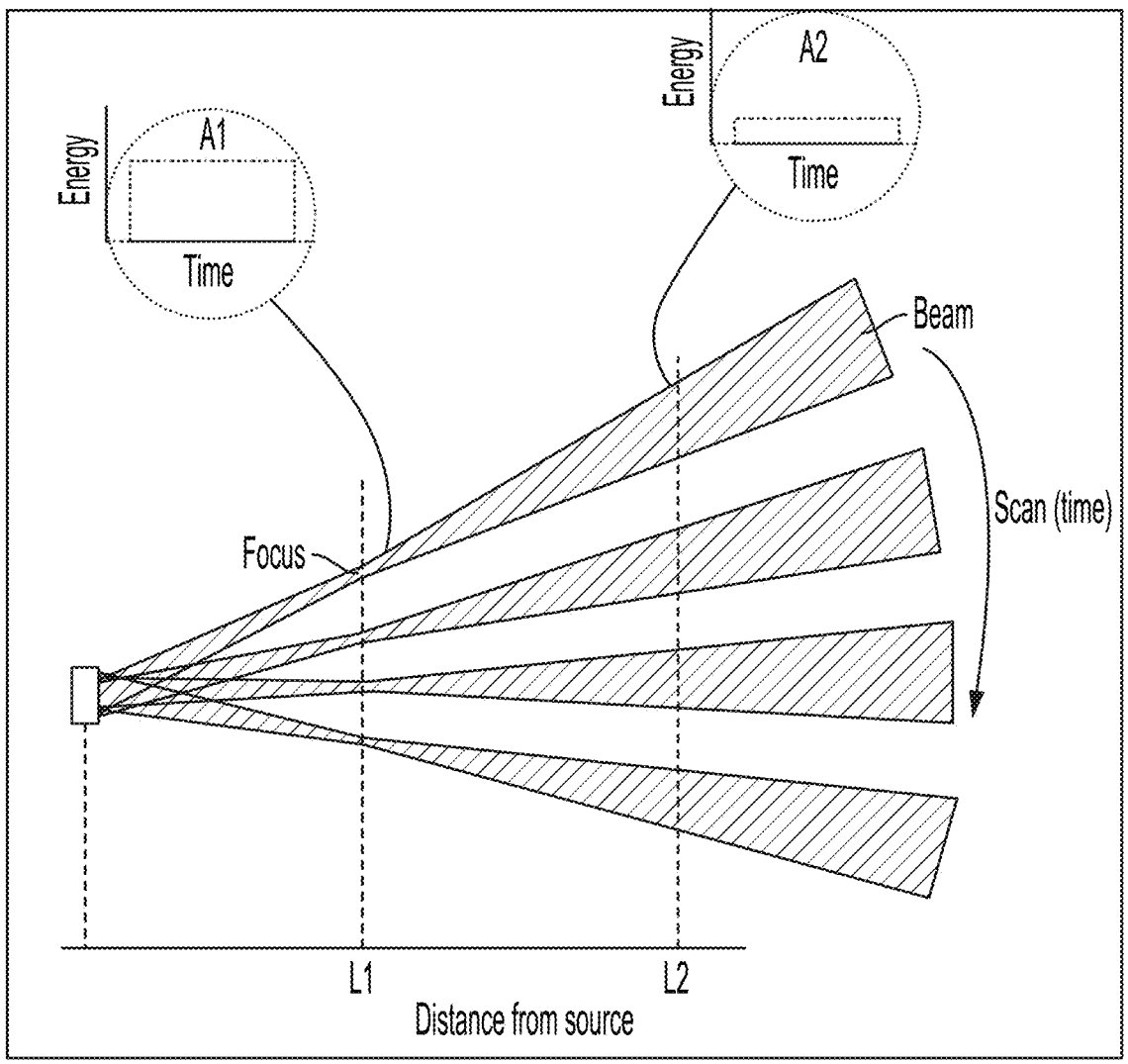
FIG. 7 depicts an alternative approach for obtaining diverging beams beyond a certain distance.

An alternative approach for obtaining diverging beams is illustrated in FIG. 7. Here focused beams are used. The focal length is chosen to be consistent with the size of the desired protected area and its distance from the source. But at all distances beyond L1, the beams will diverge.

Returning to FIGS. 2 and 3, the RF power density should be selected such that it will be sufficient to kill or deactivate pathogens within the volume 60 (i.e., between the antenna 50 and the outer boundary 65) while at the same time complying with applicable regulations. The allowable RF energies at different frequencies in $mW/cm^2$ and the relevant exposure times in minutes are noted in FIG. 1.

The apparatus 10 may be used to protect people or animals from pathogen infection in a variety of scenarios. These include direct protection of people or animals and the prevention of penetration of viruses into a specific environment or compartment. The Apparatus 10 can be used to establish a protective zone that destroys viruses that reach it or pass through it.

FIGS. 8A and 8B depict two examples of approaches for positioning the apparatus 10 to protect a person from pathogens that enter the human body via the nose, mouth, or eyes. In these situations, a device that establishes a protective zone in the vicinity of the user's face provides an effective preventive means. In the FIG. 8A embodiment, the apparatus 10 is mounted on a headband and aimed downward. In the FIG. 8B embodiment, the apparatus 10 is mounted on a necklace and aimed upwards. In alternative embodiments (not shown) the apparatus may be mounted on another part of a person's body (e.g. near the waist on a belt). These same positionings of the apparatus 10 may also be used when an infected person uses the apparatus 10 to reduce the chance of infecting others.

Figure 9:
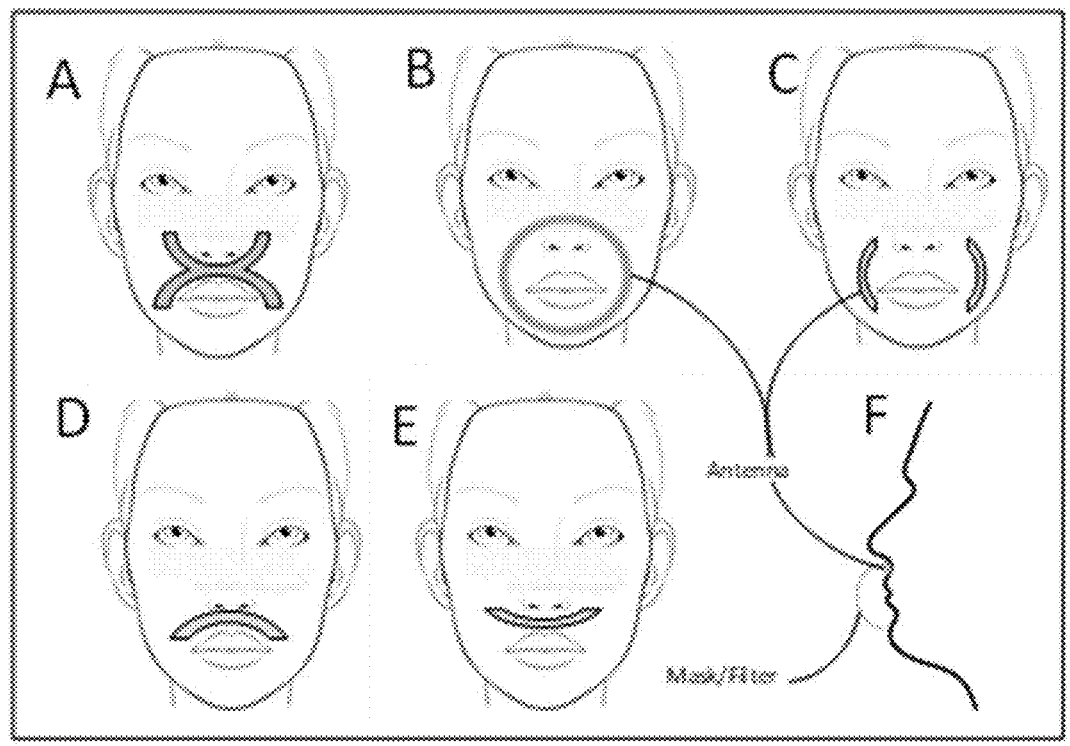
FIG. 9 depicts a variety of alternative approaches for positioning the phased array antenna in the FIG. 2 embodiment.

In alternative embodiments, the phased array antenna 50 may be positioned on a user's face (e.g., in any of the shapes and positions depicted in FIG. 9). In these embodiments, the remaining components depicted in FIG. 2 (e.g., the RF signal generator 30, the controller 20, the battery 15, etc.) may be positioned in a module that is connected to the phased array antenna 50 via an appropriate cable. An appropriate user interface may be provided to select the beam power, distance, scan spread—protective screen dimensions, etc. This user interface may be implemented using a handheld or other remote controller that can optionally be equipped with a display of the various parameters and the sensor readings.

In other alternative embodiments (not shown) the apparatus 10 may be used to protect entrances to a room or enclosure by positioning the volume 60 to cover entrances such as openings, doors, windows, etc. It can be handheld or mounted on a support that enables aiming at a selected target. The RF beam can also be directed towards surfaces or objects to affect the pathogens on or in them.

The apparatus 10 may also be incorporated within airflow ducts or other ventilation systems. In such cases care should be taken that the effective beam width is sufficiently large so that pathogens passing through the corresponding passage will reside in the passage for enough time to impart enough energy to kill or deactivate the pathogens. This can be adjusted on the basis of flow velocity measurements. In these embodiments, the power may be increased dramatically (as compared to the embodiments described above) because people are not expected to encounter the beam.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. An apparatus for killing or deactivating pathogens within a volume of air, the apparatus comprising an RF signal generator that generates a first RF signal at a frequency F, wherein the frequency F is between 1 and 20 GHz;

a plurality of phase shifters, wherein each of the phase shifters inputs the first RF signal and outputs a phase-shifted version of the first RF signal at a respective output, wherein an amount of phase shift introduced by each of the plurality of phase shifters is controllable based on a state of at least one control input;

a phased array antenna having a plurality of microwave radiators, wherein each of the respective outputs of the plurality of phase shifters drives a respective one of the plurality of microwave radiators; and a controller programmed to control the state of the at least one control input so that the plurality of phase shifters drives the phased array antenna such that a beam of RF energy emanates from the phased array antenna and sweeps through a volume positioned in front of the phased array antenna, the volume having an outer boundary with an area A, wherein the beam has an area B, an irradiance flux density D, and a speed V, all measured at the outer boundary, wherein B and D are large enough and V is small enough such that each voxel in the volume is irradiated by the beam of RF energy for enough time during each scan to kill or deactivate pathogens suspended within the volume, and wherein D and a ratio of B/A are small enough so that the power density measured at the outer boundary, averaged over time, is (a) less than F/300 $mW/cm^2$ and (b) less than 5 $mW/cm^2$.

2. The apparatus of claim 1, wherein D and a ratio of B/A are small enough so that the power density measured at the outer boundary, averaged over time, is (a) less than F/1500 $mW/cm^2$ and (b) less than 1 $mW/cm^2$.

3. The apparatus of claim 1, wherein B and D are large enough and V is small enough such that each voxel in the volume is irradiated by the beam of RF energy for enough time during each scan to heat pathogens suspended within the volume by at least 50° C.

4. The apparatus of claim 1, wherein the outer boundary of the volume is at least 10 cm away from the phased array antenna.

5. The apparatus of claim 1, wherein the outer boundary of the volume is at least 30 cm away from the phased array antenna.

6. The apparatus of claim 1, wherein B and D are large enough and V is small enough such that each voxel in the volume is irradiated by the beam of RF energy for enough time during each scan to heat microdroplets suspended within the volume by at least 50° C., wherein the microdroplets include (i) pathogens and (ii) water, and wherein the microdroplets are small enough to remain suspended within the volume.

7. The apparatus of claim 1, wherein B and D are large enough and V is small enough such that each voxel in the volume is irradiated by the beam of RF energy for enough time during each scan to heat microdroplets suspended within the volume by at least 50° C., wherein the microdroplets include (i) pathogens and (ii) water, and wherein the microdroplets have volumes of less than $10^{-12}$ Liter.

8. The apparatus of claim 1, wherein the beam of RF energy sweeps through the entire volume positioned in front of the phased array antenna at least once per second.

9. The apparatus of claim 1, wherein the beam of RF energy sweeps through the entire volume positioned in front of the phased array antenna at least 100 times per second.

10. The apparatus of claim 1, wherein the RF signal generator comprises a circuit that generates a low-power RF signal and an amplifier configured to generate the first RF signal by amplifying the low-power RF signal.

11. The apparatus of claim 1, further comprising a battery, wherein the RF signal generator, the plurality of phase shifters, and the controller are powered by the battery.

12. The apparatus of claim 1, wherein the pathogens comprise bacteria.

13. The apparatus of claim 1, wherein the pathogens comprise viruses.

14. An apparatus for killing or deactivating pathogens within a volume of air, the apparatus comprising an RF signal generator that generates a first RF signal at a frequency F, wherein the frequency F is between 1 and 20 GHz;

a plurality of phase shifters, wherein each of the phase shifters inputs the first RF signal and outputs a phase-shifted version of the first RF signal at a respective output, wherein an amount of phase shift introduced by each of the plurality of phase shifters is controllable based on a state of at least one control input;

a phased array antenna having a plurality of microwave radiators, wherein each of the respective outputs of the plurality of phase shifters drives a respective one of the plurality of microwave radiators; and a controller programmed to control the state of the at least one control input so that the plurality of phase shifters drives the phased array antenna such that a beam of RF energy emanates from the phased array antenna and sweeps through a volume positioned in front of the phased array antenna, the volume having an outer boundary, wherein the beam has a total power of $P_B$, a width in the scanning direction of $W_B$, and a sweep velocity of V, all measured at the outer boundary, wherein a single pathogen positioned at the outer boundary has a cross section area of $A_P$, and wherein the amount of RF energy that must hit a single pathogen in order to destroy that single pathogen is $E_D$, wherein $V<A_P P_B/W_B E_D$, and wherein the power density measured at the outer boundary, averaged over time, is (a) less than F/300 $mW/cm^2$ and (b) less than 5 $mW/cm^2$.

15. The apparatus of claim 14, wherein the power density measured at the outer boundary, averaged over time, is (a) less than F/1500 $mW/cm^2$ and (b) less than 1 $mW/cm^2$.

16. The apparatus of claim 14, wherein the pathogens comprise bacteria.

17. The apparatus of claim 14, wherein the pathogens comprise viruses.

* * * * *